US012721619B2

(12) United States Patent
Martinez-Alcalá Garcia et al.

(10) Patent No.: US 12,721,619 B2
(45) Date of Patent: Sep. 1, 2026

(54) THREAD SUTURING ENDOSCOPIC DEVICE

(71) Applicant: CHAIRMONKEY, S.L., Seville (ES)

(72) Inventors: Alvaro Martinez-Alcalá Garcia, Seville (ES); Felipe Martinez-Alcalá Garcia, Seville (ES)

(73) Assignee: CHAIRMONKEY, S.L., Seville (ES)

( * ) Notice: Subject to any disclaimer, the term of this patent is extended or adjusted under 35 U.S.C. 154(b) by 128 days.

(21) Appl. No.: 18/836,714

(22) PCT Filed: Feb. 6, 2023

(86) PCT No.: PCT/ES2023/070063
§ 371 (c)(1),
(2) Date: Aug. 7, 2024

(87) PCT Pub. No.: WO2023/148422
PCT Pub. Date: Aug. 10, 2023

(65) Prior Publication Data

US 2025/0143691 A1 May 8, 2025

(30) Foreign Application Priority Data

Feb. 7, 2022 (ES) ............................... ES202230088

(51) Int. Cl.
*A61B 17/04* (2006.01)
*A61B 17/062* (2006.01)

(52) U.S. Cl.
CPC ...... *A61B 17/0469* (2013.01); *A61B 17/0467* (2013.01); *A61B 17/062* (2013.01)

(58) Field of Classification Search
CPC ............ A61B 17/0469; A61B 17/0467; A61B 17/04882; A61B 17/062; A61B 17/0625
See application file for complete search history.

(56) References Cited

U.S. PATENT DOCUMENTS 6,224,614 B1 * 5/2001 Yoon .................... A61B 17/062 606/147
2013/0282031 A1 10/2013 Woodard, Jr. et al.
2015/0209028 A1 7/2015 Sniffin et al.
2017/0071597 A1 * 3/2017 Gorski ............. A61B 17/06166

FOREIGN PATENT DOCUMENTS

EP 2462877 A2 6/2012
WO 2008058005 A2 5/2008
WO 2017044838 A1 3/2017
WO 2023148422 A1 8/2023

* cited by examiner

*Primary Examiner* — Diane D Yabut
(74) *Attorney, Agent, or Firm* — HOLZER PATEL DRENNAN

(57) ABSTRACT

Suturing device for endoscopic use comprising a proximal end and a distal end, the distal end being provided with a clamp (3) formed by two facing blades (3*a,* 3*b*) intended to house a suture needle (9) and where the proximal end is provided with control mechanisms for opening and closing said clamp and changing the orientation of the needle and passing it from one blade to another of the clamp (1, 2*a,* 2*b*). Thanks to the change in orientation of the needle, it is possible to use much larger needles than in the current state of the art.

4 Claims, 6 Drawing Sheets

THREAD SUTURING ENDOSCOPIC DEVICE

CROSS-REFERENCE TO RELATED APPLICATIONS

This application is a § 371 national phase filing of International Patent Application No. PCT/ES2023/070063 filed Feb. 6, 2023, entitled "THREAD SUTURING ENDOSCOPIC DEVICE", which is related to and claims priority to Spanish Patent Application No. P202230088 filed Feb. 7, 2022, entitled "THREAD SUTURING ENDOSCOPIC DEVICE." The entire disclosures of each of the foregoing are incorporated by reference herein.

TECHNICAL SECTOR

The present invention belongs to the sector of medical-surgical equipment and more specifically to that of flexible endoscopic devices. It refers to a device for performing simple or continuous sutures of lesions or perforations applicable to all layers of the wall of a hollow body organ, such as those of the digestive tract, performed from within the organ.

BACKGROUND OF THE INVENTION

Endoscopic procedures for the diagnosis and treatment of digestive pathologies, of the biliary tree, the vascular system and other organs of the human body have developed to become procedures common to all hospitals and medical centers. Digestive endoscopy is a diagnostic-surgical technique that is practiced through natural orifices of the digestive system, the mouth or the anus, using the assistance of flexible endoscopes of different characteristics and lengths that are equipped with a light source, a video camera and a working channel smaller than 5 mm, through which different tools can be inserted. All of this allow the medical team the endoluminal diagnosis of the pathology and its treatment. These techniques are known as minimally invasive, since they avoid large interventions and therefore allow a recovery period with much fewer comorbidities, shorter and more comfortable for the patient, even without scars since no incisions are made in the skin.

The endoscopic treatment of lesions currently covers a variety of techniques such as electrical cauterization, laser photocoagulation, thermotherapy by application of heat probes, sclerotherapy, or resection techniques, either using hot or cold loops with which to perform polypectomies or mucosectomies, or elastic bands to perform musectomies and small submucosectomies. The knives that have been developed in recent years allow, on the other hand, to perform much broader or deeper resections, even making complete resections of the digestive tract wall possible in recent years.

However, this great development of resection techniques has not been accompanied by sufficient development in the techniques to close these scars or defects in the wall and therefore the real possibilities of the previously described techniques have been limited. In many cases, hemostatic clips in multiple sizes are being used to a greater or lesser extent, or those known as "Endo-loops", preformed ties that can be closed from a distance, very useful for pedicled lesions or in combination with hemostatic clips. However, these traditional systems are not sufficient for complete wall closure. For this reason, new forms of approximation are being investigated, either with techniques combined with laparoscopy, which determines the need for surgical intervention, or with devices that close the lesion before cutting it, which due to their design limit the size of the lesions to about 2 cm. Finally, some suture systems have appeared that, although useful, have multiple limitations that must be resolved. The most notable would be the one described in application US 20120157765 A1, which has great limitations in mobility, due to the need to use a cap with the needle at the distal end of the endoscope (end farthest from the operator/endoscopist), which limits the flexibility and vision, making it practically impossible to use it in the right colon (cecum, ascending colon, or transverse colon), as well as requiring a double-channel endoscope and complex operation by the endoscopist and assistant, which has limited its diffusion. Other systems that are currently being tested allow its use through endoscopes with a single working channel, but it is still necessary to place a cap to carry the needle. In addition, these suturing systems only allow one stitch to be given and the entire device must be changed if it is to be used again.

In recent years, various devices have been developed that try to solve this problem by using only the working channel to perform the suture and getting rid of the need for overtubes, caps, or material that runs outside the endoscope. Among these devices, the one described in application EP3357432A2 stands out, which, however, has encountered great difficulty when it comes to its applicability, since the size of the working channel (less than half a centimeter), the need for great flexibility to pass through the angulations of the digestive tract and the necessary manipulation of the device at a great distance from the effector area, condition the device, especially the size of the needle, which must be less than 2 mm in its long axis, which limits the strength of the suture, the efficiency and reliability when performing the suture, and therefore also limiting the size of an area that can be treated.

SUMMARY OF THE INVENTION

The purpose of the invention is to provide a flexible endoscopic suture accessory that allows easy approach to the lesion, wound or perforation (intentional or accidental), with unrestricted maneuverability and flexibility that allows loops of up to 360° to be overcome that are generated with the endoscope, even 2 meters long, during the endoscopic exploration, a simple operation for its external handling and the use of the accessory through a single working channel that, as mentioned above, is less than 5 mm. In addition, the accessory of the invention is not limited by the size or physical characteristics of the lesion when addressing the treatment, since it allows easy recharging without having to remove the endoscope, nor does it have the need to use a needle carrier cap. It also solves the issues derived from the channel work size allowing a suturing needle twice the length of the channel size and thanks to the changes in the mechanisms it also facilitates a needle thickness increase allowing to increase the tension held in the closing of the lesions.

The invention solves the problems set forth above thanks to its ability to change the alignment of the needle from a position parallel to the longitudinal axis to a position transverse to said axis. To this end, the invention proposes a suturing device for endoscopic use that comprises a first distal end (intended to carry the needle and therefore the end furthest from the operator) and a proximal end (the one intended to carry the controls for handling the needle). At the proximal end of the device are the control mechanisms, comprising sliding tabs and metal cables, which comprise various materials such as nitinol, steel, iron, that meet the characteristics of flexibility and hardness in their longitudinal axis. These cables are attached to a distal end clamp and a needle clamp mechanism in the distal end clamp. Thanks to the use of these tabs that open and close a clamp through the cables, it is possible, together with the needle clamping mechanism, to change the orientation of the latter so that when the closed device is inserted inside the patient, the needle is parallel to the main axis of the device and when they are in position to start the stitch, it is placed in a transverse position, subsequently passing from one blade to another of the clamp.

More particularly, the invention is a suturing device for endoscopic use comprising a proximal end and a distal end, the distal end being provided with a clamp formed by two facing blades intended to house a suture needle and where the proximal end is provided with control mechanisms for the opening and closing of said clamp and changing of orientation of the needle and its passage from one blade to another of the clamp. To hold the needle, each blade has a guillotine that slides on its blade and a hole to house the outside of the needle, so that the cooperation between the guillotine and the hole make it possible to hold the needle and change it from one blade to another. Optional aspects of the invention are defined in the dependent claims.

BRIEF DESCRIPTION OF THE FIGURES

To complement the description that is being made and in order to help a better understanding of the characteristics of the invention, a set of drawings is attached as an integral part of said description, where, with an illustrative and non-limiting nature, the following has been represented.

DETAILED DESCRIPTION OF THE INVENTION

Next, the preferred embodiment of the invention is described in detail, although not in a limiting way.

Figure 1:
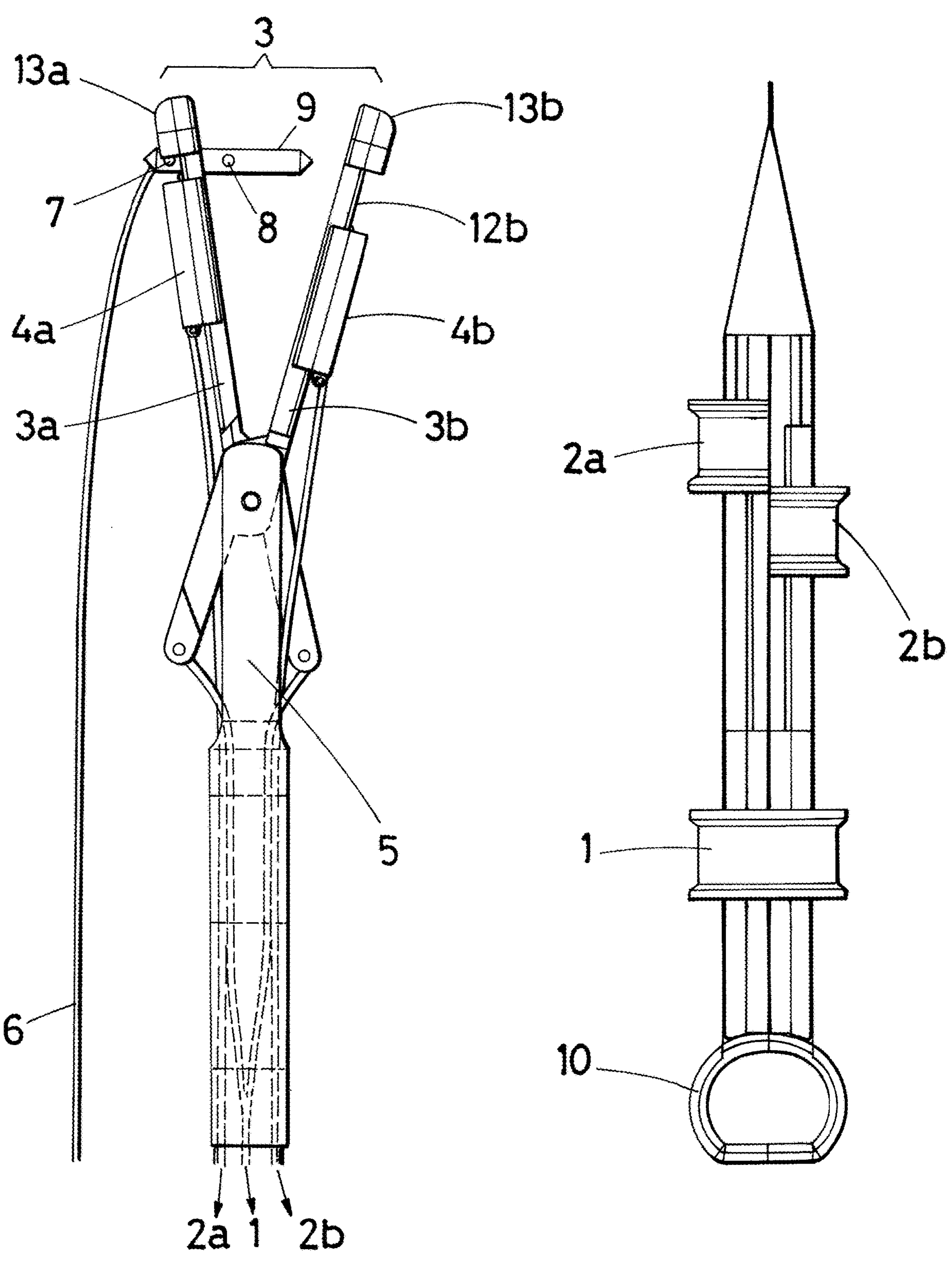
FIG. 1.—Shows a general and schematic vision of the device where it can be seen both its ends.

As it can be seen in FIG. 1, the device is structured in two well-differentiated ends, separated from each other with a sufficient length to allow its use in gastroscopes and colonoscopes, (between 180-240 cm) a proximal end closer to the operator and a distal one where the needle is located. The main characteristic of the invention is that of allowing the change of alignment of the needle, from a position parallel to the blades of the clamp to another transverse position. Thanks to this system, enough space is left for the size of the needle to be substantially larger than that of the state of the art, reaching up to 5-7 mm in length on the long axis and 0.4-0.8 mm thick, allowing greater control, fewer errors in the exchange within the stitches and allowing to apply a greater force of tension and a stitch in deeper or fibrotic tissues. Allowing likewise to maintain its mobility and flexibility in the longitudinal axis.

At the proximal end (end of the device that is closest to the user and farthest from the lesion) are the controls for operating the device. This end comprises a tubular body with a cylindrical or rectangular section, preferably made of plastic material. Neither the diameter nor the morphology of this body are limited by the space of the endoscope's working channel, since this end never enters the endoscope. Therefore, its measurements can vary between 3-7 cm in transverse diameter and between 10-25 cm in longitudinal diameter, depending on the comfort for the operator. A series of sliding tabs move on this body, a tab (1) to control the opening of the clamp (3) and two tabs to control the clamping and portability mechanism of the needle from one blade of the clamp to the other (2*a,* 2*b*) that when moving proximally or distal cables pull or push, preferably metal, which transmit the movement towards the distal end, avoiding the deformation phenomena typical of plastic materials. When the tab (1) moves towards the distal end, the blades separate and therefore the clamp (3) opens. When the operator pulls towards the proximal end, the clamp (1) closes, bringing the two blades closer together. When the tab (1) moves towards the distal end, the blades separate and therefore the clamp (3) opens. When the operator pulls towards the proximal end, the clamp (1) closes, bringing the two blades closer together. When the tab (1) moves towards the distal end, the blades separate and therefore the clamp (3) opens. When the operator pulls towards the proximal end, the clamp (1) closes, bringing the two blades closer together.

The clamping and portability mechanism of the needle comprises two sliding tabs (2*a,* 2*b* each independent with differentiated cables and independently controlling a guillotine (4*a,* 4*b*) so as to move it over the blade therefore leaving the needle free or fixed to the corresponding blade. In one embodiment these mechanisms could be provided with a stop, ledge or lock activating when the guillotine is in a clamping position preventing its involuntary opening, releasing the operator from the burden to continually apply closing force. In other of the implementations, these mechanisms of clamp opening and clamping and portability of the needle could be separated in two independent bodies, since thanks to the fact that the size of the proximal end is not limited, it is possible to have two cylindrical bodies each with one of the mechanisms and connected with the corresponding metal cables to its mechanism of action, so that they can be controlled by two operators (doctor and assistant, for example). These bodies would be joined later in the cylindrical body connecting with the proximal end.

In the proximal part of the cylindrical body, a hollow circumferential area (10) of at least 3 cm in diameter is incorporated, preferably but not necessary, where the operator inserts the thumb, in the traditional way of endoscopic devices to give stability to the device and precision to movements. The opposite end of the distal part of the device tapers to provide a transition between the proximal part where the control mechanisms are located and the proximal part, intended to be inserted into the working channel of the endoscope and typically having a diameter less than 4 mm. In this conical region the metal cables transmitting the movement generated in the controls come together.

The union between the proximal and distal ends is made by metal cables, which may or may not be covered with a plastic material of PVC, polypropylene, silicone, to reduce the resistance between the cables and group all the metal cables in a single tubular section.

Figure 3:
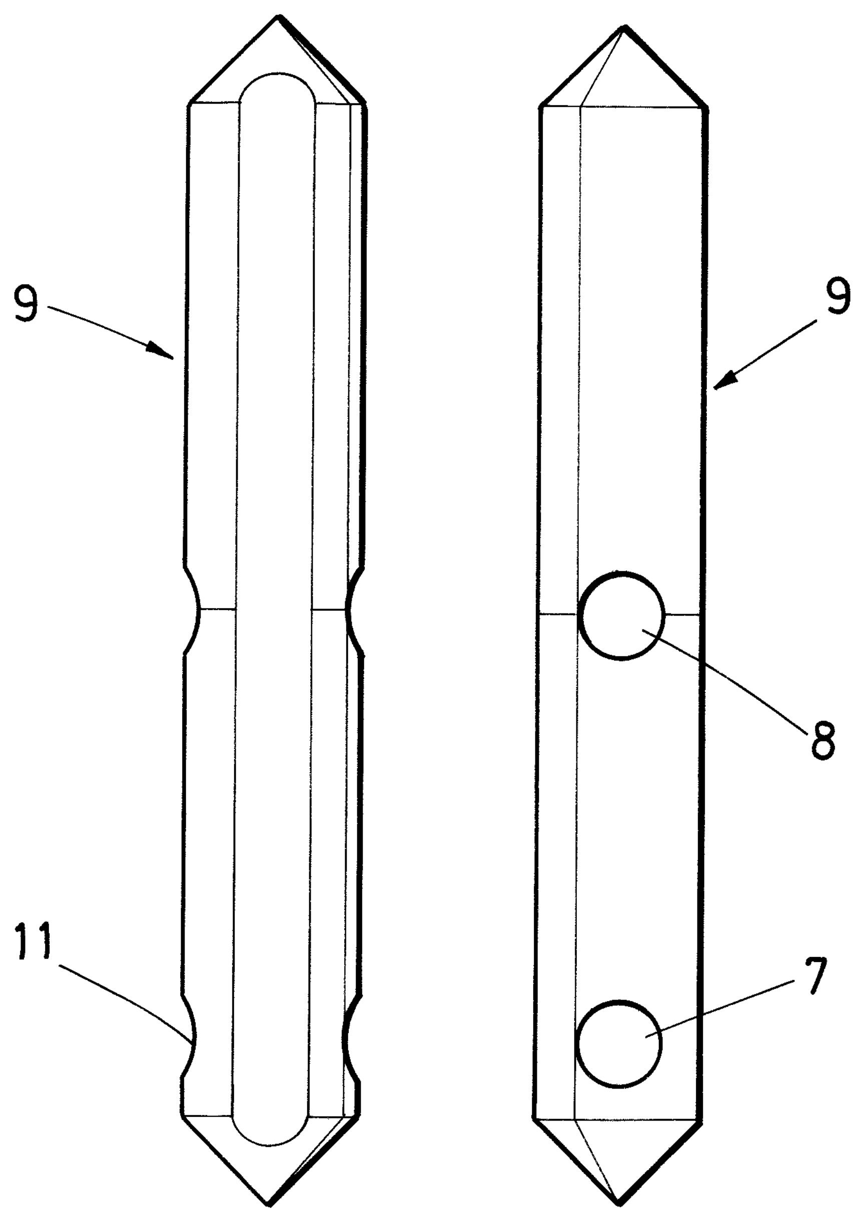
FIG. 3.—Shows a needle suitable for use in the invention.

To carry out the suture, a nylon thread, biocompatible materials or metal compounds will be fixed to the needle. The fixation of the thread can be carried out in a central area (8) (a hole or area for gluing the suture thread, FIG. 3). Optionally, the body (9) can have a coil to collect the suture thread. The coil could have a self-tensioning system that allows the thread to always have a certain tension and prevent it from becoming entangled in the movements of the endoscope.

It can be seen a diagram of the clamp (3) and the parts making it up: blades and cylindrical support (5). The blades are two equal structures facing each other and will carry the needle. They each consist of a differentiated body in two flat segments and perpendicular to each other. Both blades are attached in the form of an X to the cylindrical support (5) and share an axis that passes through said support. Each blade is attached at its proximal end to a metal cable and these cables are attached to the sliding drive tab (1). Since the blades are arranged in an X-shape and can rotate around the axis that passes through the support, the clamp (3) can be opened and closed with a single movement of the drive tab (1).

The cylindrical support (5) has a cylindrical proximal part that is attached to the tubular body and which in turn allows the passage of the cables to control the opening and closing of the clamp. In an initial configuration, it could have specific holes for this, although in another configuration it could be arranged in a single larger hole. At the end attached to the blades, it is U-shaped to allow them to rotate.

Figure 2:
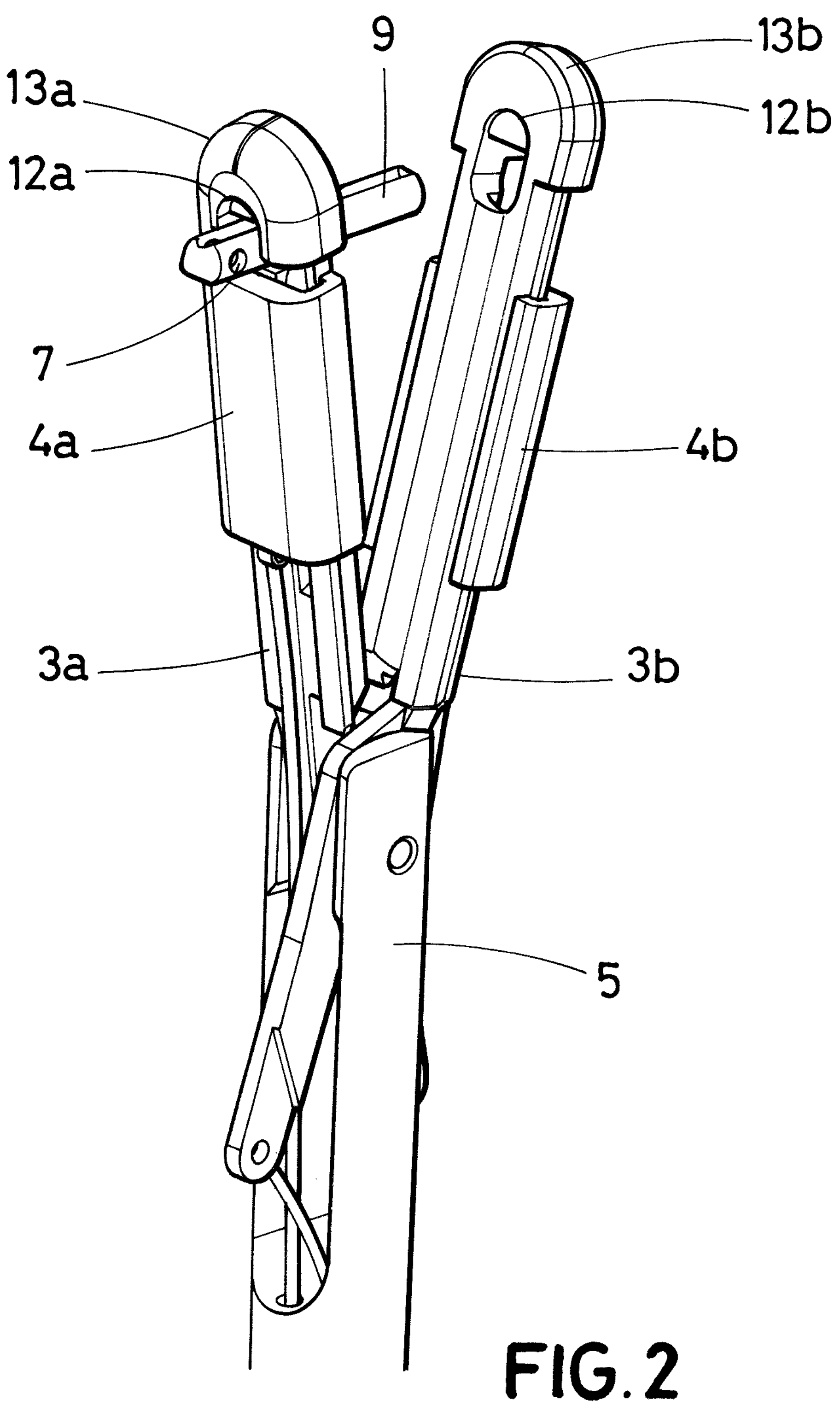
FIG. 2.—Shows a general and schematic view of the device of the invention with the opening and closing system open and the needle in a transverse position.

As it can be seen in FIG. 2, the guillotine (4*a,* 4*b*) is moved from the outside over the distal segment of the blades. The guillotine is attached to the outside of the segment by means of a rail system that holds both pieces together, but allowing movement along the segment when the metal cables controlled by the sliding tabs are activated. In the inner part of this segment, in both blades, there is a thinner rail where the needle is housed at the time of introduction through the endoscope's working channel and prior to changing direction and positioning for suturing.

Referring to FIG. 2, the device can be seen once the needle (5) has been placed in a transverse position and is fixed by the guillotine of the left blade (4*a*), with the corresponding sliding tab (2*a*) displaced. In this figure the thread for the change of orientation (6) no longer appears since once the needle is positioned it is withdrawn to avoid interference with the suture thread. In this figure the clamp (3) is seen in the open position.

To change the orientation of the needle, in one implementation there is a round-trip thread (6) that passes through a specific hole in the needle and later through the hole in one of the blades of the clamp to run externally through the device. Said thread is controlled at the proximal end. The thread is preferably nylon, it starts from the proximal end of the device, runs through the body (externally in the figures, although it can also be inside the body itself parallel to the metal cables of the clamp opening and holding system and portability of the needle) and subsequently passes through the hole of one of the blades of the clamp, (12) and through a lateral hole of the needle (7), returning to the proximal end of the device. By pulling both ends of the thread (6) at the same time, the needle changes its orientation and is inserted into the blade through the hole (12*a,* 12*b*), thus remaining in a transverse position. Once in this position, the clamping mechanism is activated, that is, the guillotine of the corresponding blade (4*a* or 4*b*) slides through the corresponding sliding tab (2*a,* 2*b*), thus fixing the needle to the blade. Once fixed, the thread (6) is withdrawn by pulling one of the ends of the thread that runs to release the needle from this system and leaving it free so that it does not interfere with subsequent suturing.

There are other optional ways to carry out this change of orientation, among which stands out, in a suggesting but not limiting way, the introduction of ferrous material at one of the ends of the needle and magnetization of one of the blades so that when they are opened they are placed by magnetic attraction in a transverse position similar to a screw in a magnetized screwdriver.

In the distal part of this segment there is a hole for the passage of the needle (12). This hole will have the appropriate size for the passage of the needle, which in the preferred embodiment will be 0.6 mm. At the distal end of the blade is the blade stop (13), this stop is thicker than the rest and it is the sum of the thickness of the blade plus the guillotine. The function of the stop is to allow the guillotine to exert pressure on it, keeping the needle in position. It preferably has a rounded and polished end that facilitates insertion through the working channel and reduces abrasions that could be caused by rubbing against the tissue when performing the suture.

In other embodiments, this stop (13) is provided with a hole in the upper part to introduce a stylet that complements the guillotine and that would pass the needle through a hole to improve fixation at the exact point.

In another of the possible implementations, the stops (13) of the blades would have a base so that the guillotine can cut the thread, in a configuration in which the needle position change thread is not withdrawn but cut.

The needle, (9), therefore, is configured in its preferred embodiment (FIG. 3) in a cylindrical body that is bevelled and conical at both ends and with a lateral guide recess or recesses, shown in the figures, since the stitch will be carried out in both directions, with the suture thread attached to the central point of the same (8), in the preferred embodiment it is represented as a hole since the thread could be tied, stuck or joined in any way that is considered as part of the state of the technique. The thread can be made of biocompatible material, nylon, metal, biodegradable, etc.

Likewise, the needle has a hole (7) on one of the sides prior to the bevelled area through which the thread (6) in charge of changing direction passes. The needle can have a narrow area on both sides (11) (prior to the bevelled area) as a neck, so that the guillotine can use that area as a fixing point when performing the stitch.

Figures 4A, 4B:
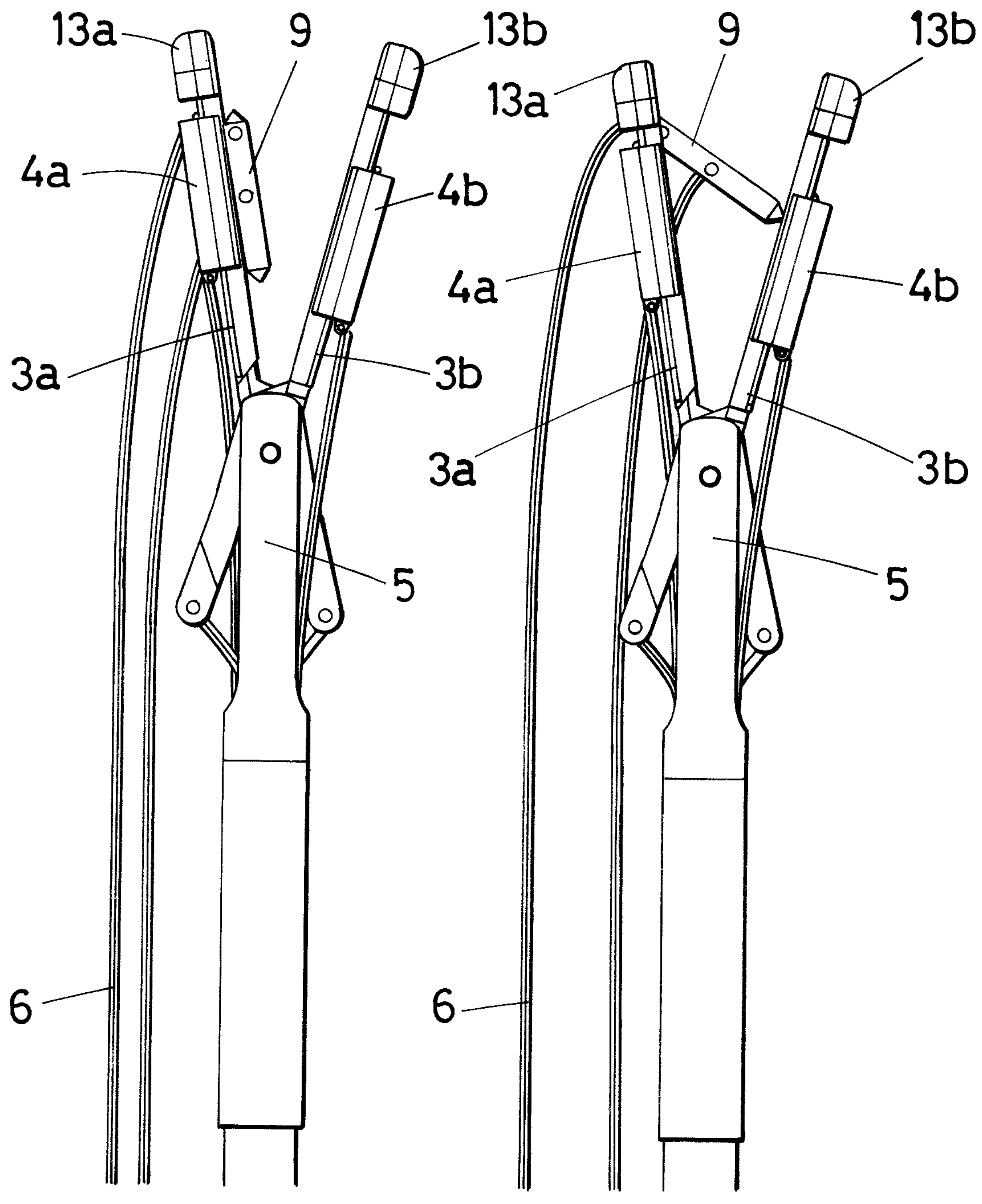
FIG. 4.—Shows the distal end, that is, the one closest to the lesion and the different steps of opening, closing and changing the orientation of the needle to give a stitch.
Figures 4C, 4D:
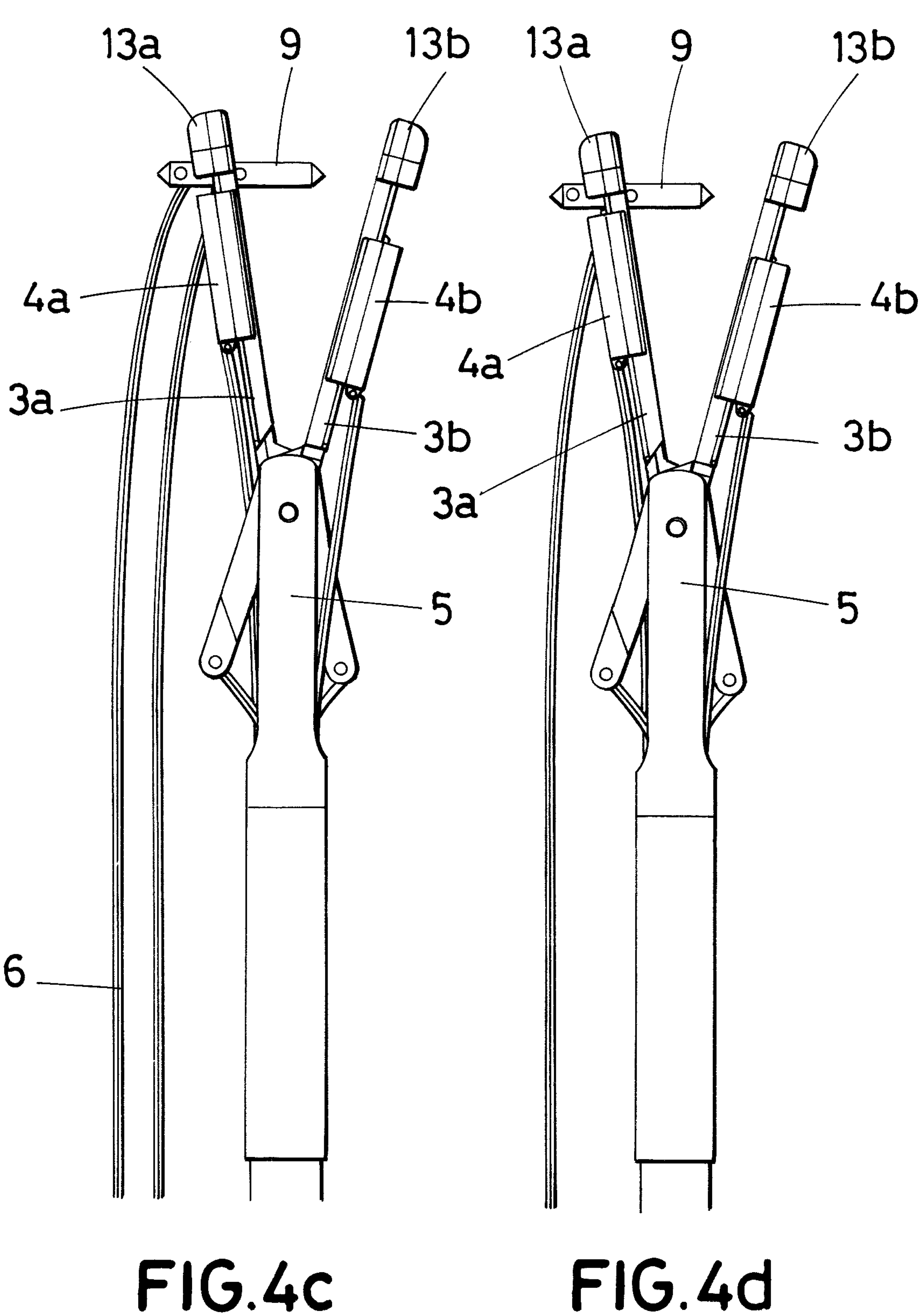
Figures 4E, 4F:
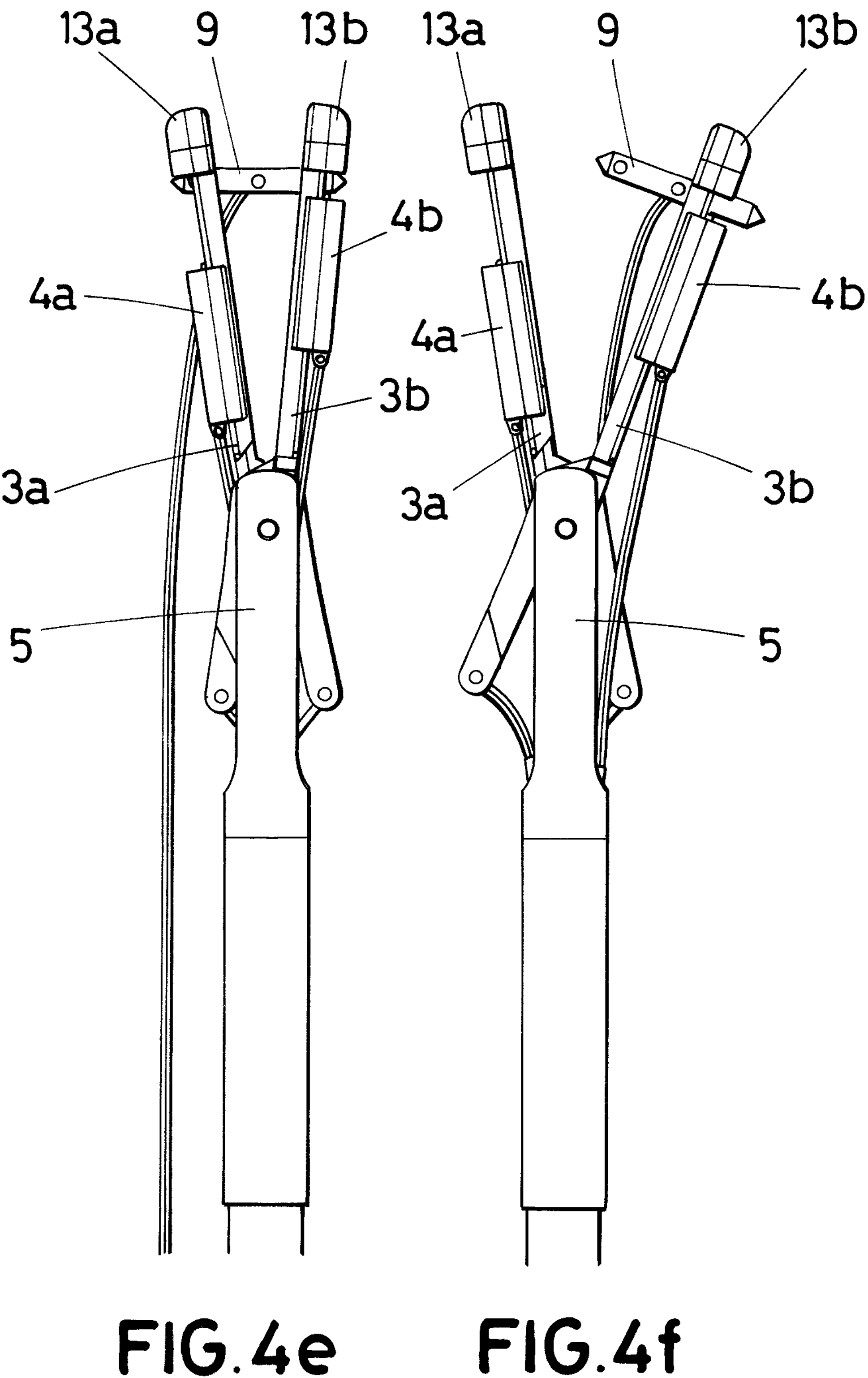

In FIG. 4 it can be seen the suturing process schematically, separated into various steps for a better understanding.

The first step (FIG. 4*a*) consists of introducing the invention through the working channel of the endoscope in the closed position (in the figure it appears slightly open for a better understanding of the relative positions of the needle and the blades).

The second step (4*b*) consists of opening the blades. To do this, the tab of the clamp opening system (1) is moved towards the distal end. The tab displaces two cables equally toward the distal end. As the cables are attached to the blades, they rotate on the axis. At this same moment, the orientation change of the needle (9) is carried out from its position parallel to the blade to the transverse position. To do this, in the preferred configuration, both ends of the wire (6) are pulled, which, starting from the proximal end of the operator, passes through one of the holes in one of the blades (12*a*), and later through the specific hole of the needle (7) until the needle is transverse to the device.

In the third step (4*c*) the needle is fixed or secured to the guillotine (4*a,* 4*b*) by means of the control tabs of the clamping mechanism (2*a,* 2*b*). The operator respectively moves one or the other tab, each tab being connected to an independent cable for each guillotine. Once the needle is fixed in position, the suture is performed.

In the fourth, fifth and sixth steps (4*d*, 4*e*, 4*f*) it can be seen the needle after passing from one blade to the other, for which the opening and closing movement of the clamp (3) must be carried out using the tab (1) and toggle the control tabs (2*a*, 2*b*) to move the trimmers in order to lock or release the needle in a controlled manner. These steps can be repeated as many times as necessary to achieve the desired suture.

Subsequently, the needle is released, which will remain inside the body with the thread, which, starting from the needle, runs through each of the stitches that have been made. A knot can be made at the end of it or a system can be crimped through a cannula introducing a fastener, or any of the systems known for itches.

In view of this description and figures, the person skilled in the art will be able to understand that the invention has been described according to some preferred embodiments thereof, but that multiple variations can be introduced in said preferred embodiments, without exceeding the object of the invention as it has been claimed.

The invention claimed is:

1. A thread suturing flexible device for endoscopic use comprising a proximal end and a distal end, wherein:

the distal end is provided with a clamp formed by two facing blades intended to house a suture needle in a position parallel to a main axis of the device, the proximal end is provided with control mechanisms for the opening and closing of the clamp and changing of orientation of the suture needle to a transverse position and passing of the suture needle from one blade to another of the clamp, each blade is provided with a guillotine adapted to slide on the blade and a corresponding blade hole so that when the suture needle changes its orientation to the transverse position, the suture needle is fixed by the guillotine and the corresponding hole, and the guillotines are provided with a cutting edge.

2. The thread suturing flexible device according to claim 1, wherein the control mechanisms are a first sliding tab attached to a first metal cable, adapted to open and close the clamp and second metal cables attached to corresponding sliding tabs to move a corresponding guillotine on its blade.

3. The thread suturing flexible device according to claim 1, further comprising:

the suture needle; and a thread associated with the suture needle for changing the orientation of the suture needle.

4. The thread suturing flexible device according to claim 1, wherein each blade is provided with a stop at its distal end.

* * * * *